United States Patent [19]

Yalvac et al.

[11] Patent Number: 5,229,300
[45] Date of Patent: Jul. 20, 1993

[54] MEMBRANE METHOD FOR THE DETERMINATION OF AN ORGANIC ACID

[75] Inventors: E. Deniz Yalvac; Richard G. Melcher; Robert A. Bredeweg, all of Midland, Mich.

[73] Assignee: The Dow Chemical Company, Midland, Mich.

[21] Appl. No.: 657,229

[22] Filed: Feb. 19, 1991

[51] Int. Cl.$^5$ .............................................. B01D 15/08
[52] U.S. Cl. .................... 436/178; 436/128; 436/129; 436/131; 436/171; 210/96.2; 210/639
[58] Field of Search .................. 436/52, 61, 128, 129, 436/131, 171, 178, 179; 210/96.2, 638, 639

[56] References Cited

U.S. PATENT DOCUMENTS

| | | | |
|---|---|---|---|
| 4,775,476 | 10/1988 | Melcher et al. | 210/635 |
| 4,837,161 | 6/1989 | Stevens et al. | 436/52 |
| 4,913,821 | 4/1990 | Melcher et al. | 210/635 |
| 4,962,042 | 10/1990 | Morabito et al. | 436/161 |

FOREIGN PATENT DOCUMENTS 0370555 5/1991 European Pat. Off. .

Primary Examiner—James C. Housel
Assistant Examiner—David Redding
Attorney, Agent, or Firm—Timothy S. Stevens

[57] ABSTRACT

A chemical analysis method for the determination of a first organic acid in the presence of a second organic acid both of which are in a solution to be analyzed, the $pK_a$ of the first acid being at least 2 $pK_a$ units larger than the $pK_a$ of the second acid. The method includes three steps. The first step if to form a pH adjusted solution to be analyzed by adjusting the pH of the solution to be analyzed to be between the $pK_a$ of the first acid and the $pK_a$ of the second acid so that the first acid is predominately in its unionized form and so that the second acid is predominately in its ionized form. The second step is to partition the pH adjusted solution to be analyzed from a receiving solution with a semipermeable membrane, the semipermeable membrane being more permeable to the unionized form of the first acid than to the ionized form of the second acid, the first acid being soluble in the receiving solution so that the first acid permeates into the membrane from the pH adjusted solution to be analyzed and then permeates out of the membrane into the receiving solution. The last step is to determine the concentration of the first acid in the receiving solution so that the concentration of the first acid in the solution to be analyzed can be estimated.

12 Claims, 1 Drawing Sheet

MEMBRANE METHOD FOR THE DETERMINATION OF AN ORGANIC ACID

BACKGROUND OF THE INVENTION

Membranes have been widely used in chemical analysis methods. Cortes and Davis, U.S. Pat. No. 4,529,521, used membranes to determine components of interest in latex serum. Stevens, Jewett and Bredeweg, U.S. Pat. No. 4,751,004 used membranes to suppress an Ion Chromatography eluent. Morabito, Melcher, Hiller and McCabe, U.S. Pat. No. 4,962,042, used membranes in a Gas Chromatography and Rothman, U.S. Pat. No. 4,837,161, used membranes to add reagent to a Flow Injection Analysis carrier stream. Melcher and Burt, U.S. Pat. No. 4,913,821, used membranes in aphenol analyzer. Melcher and Cortes, U.S. Pat. No. 4,775,476, used membranes in a Liquid Chromatography system. It is known that the protonated or unionized form of an organic acid will permeate across a silicone rubber membrane at a faster rate than the ionized form of the acid.

SUMMARY OF THE INVENTION

A chemical analysis method for the determination of a first organic acid in the presence of a second organic acid both of which are in a solution to be analyzed, the $pK_a$ of the first acid being at least 2 $pK_a$ units larger than the $pK_a$ of the second acid. The method includes three steps. The first step is to form a pH adjusted solution to be analyzed by adjusting the pH of the solution to be analyzed to be between the $pK_a$ of the first acid and the $pK_a$ of the second acid so that the first acid is predominately in its un-ionized form and so that the second acid is predominately in its ionized form. The second step is to partition the pH adjusted solution to be analyzed from a receiving solution with a semipermeable membrane, the semipermeable membrane being more permeable to the unionized form of the first acid than to the ionized form of the second acid, the first acid being soluble in the receiving solution so that the first acid permeates into the membrane from the pH adjusted solution to be analyzed and then permeates out of the membrane into the receiving solution. The last step is to determine the concentration of the first acid in the receiving solution so that the concentration of the first acid in the solution to be analyzed can be estimated.

DETAILED DESCRIPTION OF THE INVENTION

Figure 1:
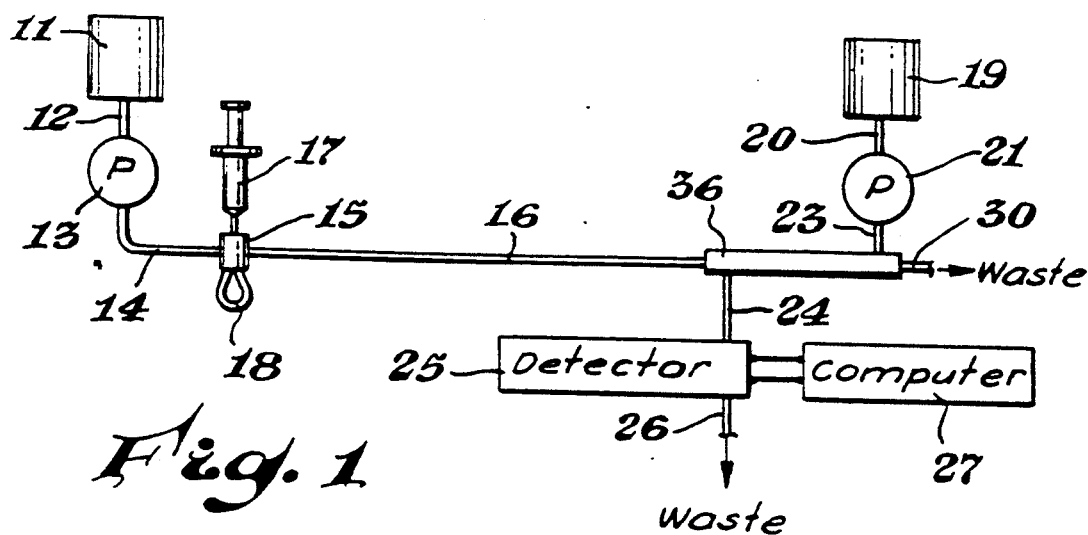
FIG. 1 is a side view, partly in full and partly schematic, of an apparatus for carrying out the method of the present invention, the apparatus including a membrane cell.

Referring now to FIG. 1, therein is shown an apparatus 10 for carrying out the method of the present invention. A reservoir 11 is used to contain a liquid buffer solution. The liquid buffer solution is conducted by a tube 12 to a pump 13. Then, the liquid buffer solution is pumped by the pump 13 through the following elements: a tube 14; a loop-type sample injection valve 15; a tube 16; a membrane cell 36; a tube 30; and finally to waste. A liquid solution to be analyzed is contained in a syringe 17. The liquid solution to be analyzed contains a first organic acid and a second organic acid, the $pK_a$ of the first acid being at least 2 $pK_a$ units larger than the $pK_a$ of the second acid. The solution to be analyzed, of course, can contain other components including other organic acids as long as it contains the above stated first and second organic acids. When the first or the second acid is polybasic, then the term $pK_a$ refers to the $pK_{a1}$ of the acid or acids. The pH of the liquid buffer is between the $pK_a$ of the first acid and the $pK_a$ of the second acid. The syringe 17 is used to fill a sample loop 18 with the solution to be analyzed. The sample loop 18 has a predetermined volume depending on its length and internal diameter. When the valve 15 is actuated, then the solution to be analyzed contained within the loop 18 is added to the flowing stream of liquid buffer flowing in the tube 16 and through the cell 36. Additionally, when the valve 15 is so actuated, then the solution to be analyzed contained within the loop 18 is pH adjusted to substantially the pH of the buffer. The valve 15 can be automatically actuated and the solution to be analyzed can be conducted to it, e.g., directly from a chemical process in an on-line analysis system. The tubing 16 must be long enough to ensure that the pH of the injected solution to be analyzed is adjusted. An in-line mixer, not shown, such as the 500 microliter mixer available from the Lee Co., can be used to ensure this adjustment. A reservoir 19 is used to contain a receiving solution. The receiving solution can be aqueous or nonaqueous. An example of an aqueous receiving solution is deionized water. An example of a nonaqueous receiving solution is heptane. The first acid must be soluble in the receiving solution and preferably the receiving solution is aqueous and has a pH at least two pH units greater than the $pK_a$ of the first acid. The receiving solution contained in the reservoir 19 is conducted to a pump 21 by a tube 20. The receiving solution is pumped by the pump 21 through the following elements: a tube 23; the membrane cell 36; a tube 24; a flow-through absorption spectroscopy detector 25; a tube 26; and finally to waste.

Figure 2:
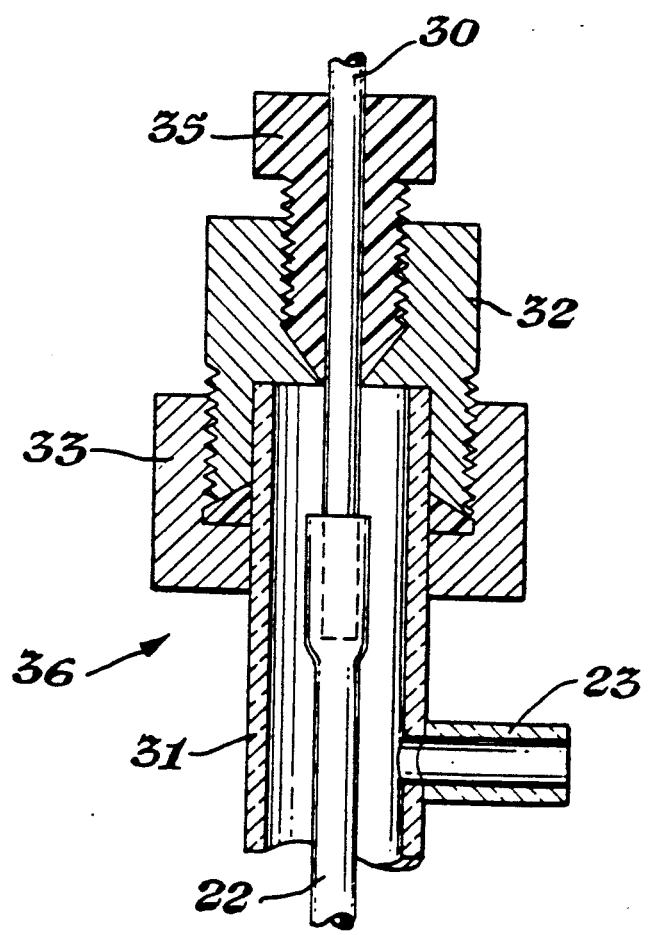
FIG. 2 is a side cross-sectional view of one end of a preferred membrane cell for use in the apparatus shown in FIG. 1.

Referring now to FIG. 2, therein is shown a cross-sectional view of one end of the membrane cell 36. The cell 36 has a one quarter inch outside diameter glass shell 31. The tube 23, also referring now to FIG. 1, is connected to the shell 31. A standard one quarter inch liquid chromatography end fitting 32, e.g., the column end fitting H6317 available from the Anspec Company, Ann Arbor Michigan, is attached to the shell 31 by a TEFLON ferrule 34, e.g., the Anspec Company TEFLON ferrule catalog number A1567, and a one quarter inch tubing nut 33, e.g., the Anspec Company nut catalog number A1426. The tube 30 is one sixteenth inch outside diameter stainless steel tubing and is positioned through a FINGERTIGHT brand fitting 35 available from the Anspec Company as catalog number H1268. The end of a tubular membrane 22 is stretched over the end of the tube 30 as shown. The membrane 22 is preferably a length of SILASTIC brand silicone rubber medical tubing from the Dow Corning Corporation of Midland Michigan, e.g., a twenty centimeter length of 0.012 inch internal diameter, 0.025 inch outside diameter SILASTIC brand tubing. It is helpful to swell the SILASTIC brand tubing in xylene when stretching it over the end of the tubing 30. When the xylene evaporates, then the membrane 22 shrinks back to its original dimensions and forms a tight seal to the tube 30. Although silicone rubber is a preferable material for the membrane of the present invention, the membrane can be made of other materials such as other rubbers or polymers as long as the membrane is a semipermeable membrane, i.e., as long as the membrane is more permeable to the protonated or unionized form of the first acid than to the ionized form of the second acid. The meaning of the term "unionized acid" and "ionized acid" will be understood by considering the following example. If one gram of phenol is dissolved in 100 milliliters of water, then the phenol is present in the water substantially in its protonated or unionized form. If one gram of sodium hydroxide is now dissolved into this phenol-water mixture, then sodium hydroxide reacts with the phenol to produce water and dissolved sodium phenate. The phenol is present in this sodium phenate solution substantially in its ionized form. The term "permeable" means the amount of an acid that permeates for a fixed time through a fixed area of a fixed thickness of a membrane at a fixed temperature into a given receiving solution when the concentration of the unionized acid is fixed. The use of a tubular membrane is not critical, e.g., a sheet type membrane can be used in a suitable membrane cell wherein the membrane partitions the pH adjusted solution to be analyzed from the receiving solution. The other end of the cell 36 is substantially identical to the end shown in FIG. 2. Therefore, when the fitting 35 is loosened, the tube 30 can be adjusted axially to take up any slack in the membrane 22 and then the fitting 35 can be tightened.

Referring now again to FIGS. 1 and 2, the receiving solution contained in the reservoir 19 is pumped by the pump 21; through the tube 23; through the space between the inside of the shell 31 and along the outside of the membrane 22; through the tube 24; through the detector 25; and then through the tube 26 to waste. The liquid buffer contained in the reservoir 11 is pumped by the pump 13: through the tube 14; through the valve 15; through the tube 16; along the inside or bore of the membrane 22; and then through the tube 30 to waste. When the valve 15 is actuated, then a predetermined volume of solution to be analyzed is added to the flowing stream of liquid buffer, adjusting its pH to substantially the pH of the buffer, and is carried to the inside or bore of the membrane 22. The first acid permeates into the membrane 22 from the pH adjusted solution and then permeates out of the membrane 22 into the flowing receiving solution surrounding the membrane 22 and is conducted to the detector 25 by the tube 24. The detector 25 must be responsive to the concentration of the first acid in the receiving solution. A preferred detector 25 is a flow through ultraviolet spectrometer such as is commonly used as a liquid chromatography detector, e.g., the Kratos SPECTROFLOW 757 variable wavelength detector available from the Anspec Company, supra, as catalog number F2757. A lower cost alternative preferred detector is the LDC/Milton Roy uv-MONITOR brand fixed wavelength detector available from the Anspec Company as catalog number F1096. The concentration of the first acid in the solution to be analyzed is a function of the response of the detector 25 which can be conveniently directed to a computer 27 for data computation and printout, e.g., in the form of a strip chart peak response as well as the peak height, peak area and computed concentration of the first acid in the solution to be analyzed. A preferred computer 27 is the Anspec AN-4270 Chromatography Integrator, Catalog number F4270. Calibration of the apparatus 10 can be made by injecting standards of known concentration. Calibration is generally effected by temperature. Thus, the apparatus 10 is best operated under constant temperature conditions. In many applications it is preferable to stop the pump 21 for a period of time at least when the injected solution to be analyzed is flowing through the cell 36 to maximize the sensitivity and precision of the method. Alternatively, a three-way valve can be plumbed into the tubing 23 so that the pump 21 remains running but its flow is directed back into the reservoir 19 while flow is stopped to the cell 36.

Referring now to FIGS. 1 and 2, the flow of liquid buffer is made along the inside or bore of the membrane 22 and the flow of receiving solution is made along the outside of the membrane 22. This arrangement, of course, is not critical and preferably the flow of liquid buffer is made along the outside of the membrane 22 while the flow of receiving solution is made along the inside or bore of the membrane 22. It will thus be appreciated that the apparatus shown in FIGS. 1 and 2 is but one of many that could have been used to carry out the method of the present invention.

EXAMPLE

A system like that shown in FIGS. 1 and 2 is assembled as described above and further herein. An Eldex Model AA-72-SF dual head pump from Anspec is used as the pump 13 and 21. The buffer is pumped at a flow rate of one milliliter per minute. The receiving solution is also pumped at a flow rate of one milliliter per minute. The injection valve 15 is a Valco Model AC6UWPHC-valve from Anspec. The loop 18 contains 100 microliters. A 500 microliter in-line mixer from the Lee Co. is used in the line 16. The detector is an LDC Model 1203, 280 nanometer wavelength, from Anspec. The 1/32 inch temperature stabilization tubing of the LDC Model 1203's flow cell is bypassed so that the back pressure through the flow cell is lowered. The cell 36 is plumbed so that the buffer flows around the outside of the membrane 22 while the receiving solution flows along the inside or bore of the membrane 22. The buffer is based on a 0.1 molar sodium phosphate solution and has a pH of 6. The receiving solution is 0.1N sodium hydroxide. The solution to be analyzed contains phenol as the first organic acid and salicylic acid as the second organic acid. The stopped flow technique described above is used and the stop time is 445 seconds, the stop time beginning just as the injected solution to be analyzed reaches the membrane cell. The total analysis cycle time is 600 seconds. Known standards containing from 500–5000 parts per million each of phenol and salicylic acid are used to calibrate the system. A solution to be analyzed is injected and the system estimates that it contains 2,646 parts per million phenol. This analysis is repeated again 84 times. The average estimated phenol concentration to the solution as 2,705 parts per million with a relative precision of 4.7 percent at the 95 percent confidence level.

What is claimed is:

1. A chemical analysis method for the determination of a first organic acid in the presence of a second organic acid both of which are in a solution to be analyzed, the $pK_a$ of the first acid being at least 2 $pK_a$ units larger than the $pK_a$ of the second acid, the method comprising the steps of:

(a) forming an aqueous pH adjusted solution by adjusting the pH of the solution to be analyzed to be between the $pK_a$ of the first acid and the $pK_a$ of the second acid so that the first acid is predominately in its unionized form and so that the second acid is predominately in its ionized form;

(b) partitioning the aqueous pH adjusted solution to be analyzed from a receiving solution with a semipermeable membrane, the semipermeable membrane being more permeable to the unionized form of the first acid than to the ionized form of the second acid, the first acid being soluble in the receiving solution so that the first acid permeates into the membrane from the pH adjusted solution to be analyzed and then permeates out of the membrane into the receiving solution; and then (c) determining the concentration of the first acid in the receiving solution so that the concentration of the first acid in the solution to be analyzed can be estimated.

2. The method of claim 1 wherein the receiving solution is aqueous and the pH of the receiving solution is larger than the $pK_a$ of the first acid.

3. The method of claim 2 wherein the $pK_a$ of the first acid is at least 4 $pK_a$ units larger than the $pK_a$ of the second acid, wherein the pH of the pH adjusted solution is at least 2 pH units lower than the $pK_a$ of the first acid and is at least 2 pH units larger than the $pK_a$ of the second acid, wherein the pH of the receiving solution is at least 2 pH units larger than the $pK_a$ of the first acid and wherein the concentration of the first acid is determined in the receiving solution by absorption spectroscopy.

4. The method of claim 3 wherein the first acid is phenol, wherein the second acid is salicylic acid and wherein the semipermeable membrane is a tubular silicone rubber membrane.

5. The method of claim 1 wherein the pH adjusted solution to be analyzed is formed by adding a preselected volume of a solution to be analyzed to a flowing stream of a pH buffer solution, wherein the pH adjusted solution to be analyzed is flowed along one side of the membrane and wherein the receiving solution is flowed along the other side of the membrane to a detector, the detector being s responsive to the concentration of the first acid.

6. The method of claim 5 wherein the receiving solution is aqueous and the pH of the receiving solution is larger than the $pK_a$ of the first acid.

7. The method of claim 6 wherein the $pK_a$ of the first acid is at least 4 $pK_a$ units larger than the $pK_a$ of the second acid, wherein the pH of the pH adjusted solution is at least 2 pH units lower than the $pK_a$ of the first acid and is at least 2 pH units larger than the $pK_a$ of the second acid, wherein the pH of the receiving solution is at least 2 pH units larger than the $pK_a$ of the first acid and wherein the concentration of the first acid is determined in the receiving solution by absorption spectroscopy.

8. The method of claim 7 wherein the first acid is phenol, wherein the second acid is salicylic acid and wherein the semipermeable membrane is a tubular silicone rubber membrane.

9. The method of claim 5 wherein the flow of receiving solution is temporarily stopped when the pH adjusted solution to be analyzed is flowed along one side of the membrane and thereafter resumed.

10. The method of claim 9 wherein the receiving solution is aqueous and the pH of the receiving solution is larger than the $pK_a$ of the first acid.

11. The method of claim 10 wherein the $pK_a$ of the first acid is at least 4 $pK_a$ units larger than the $pK_a$ of the second acid, wherein the pH of the pH adjusted solution is at least 2 pH units lower than the $pK_a$ of the first acid and is at least 2 pH units larger than the $pK_a$ of the second acid, wherein the pH of the receiving solution is at least 2 pH units larger than the $pH_a$ of the first acid and wherein the concentration of the first acid is determined in the receiving solution by absorption spectroscopy.

12. The method of claim 11 wherein the first acid is phenol, wherein the second acid is salicylic acid and wherein the semipermeable membrane is a tubular silicone rubber membrane.

* * * * *

UNITED STATES PATENT AND TRADEMARK OFFICE
CERTIFICATE OF CORRECTION

PATENT NO. : 5,229,300

DATED : July 20, 1993

INVENTOR(S) : E. Deniz Yalvac, et al.

It is certified that error appears in the above-identified patent and that said Letters Patent is hereby corrected as shown below:

Column 6, Line 1, "detector being s responsive to the concentration of the", should correctly read --detector being responsive to the concentration of the--.

Column 6, Claim 11, Line 33, "at least 2 pH units are larger than the $pH_a$ of the first acid", should correctly read --at least $2_{pH}$ units larger than the $pK_a$ of the first acid--.

Signed and Sealed this

Tenth Day of May, 1994

*Attest:*

BRUCE LEHMAN

*Attesting Officer*   *Commissioner of Patents and Trademarks*